United States Patent [19]

White

[11] 3,994,964

[45] Nov. 30, 1976

[54] PROCESSES FOR THE PRODUCTION OF CARBOXYLIC ACIDS FROM GLYCIDONITRILES

[75] Inventor: David R. White, Kalamazoo, Mich.

[73] Assignee: The Upjohn Company, Kalamazoo, Mich.

[22] Filed: Oct. 24, 1974

[21] Appl. No.: 517,462

Related U.S. Application Data

[62] Division of Ser. No. 271,389, July 13, 1972, abandoned.

[52] U.S. Cl. .................. 260/515 R; 260/293.88; 260/294.9; 260/295 R; 260/326.2; 260/326.13 R; 260/332.2 A; 260/345.2; 260/345.7; 260/347.3; 260/397.1; 260/464; 260/465 F; 260/465.6; 260/514 R; 260/514 G; 260/514 H; 260/526 R; 260/540

[51] Int. Cl.² ................. C07C 51/00; C07C 51/08

[58] Field of Search ........ 260/515 R, 526 R, 468 R, 260/465 F, 465.6, 540

[56] References Cited

UNITED STATES PATENTS 2,326,373   8/1943   Long ............................ 260/465.6

OTHER PUBLICATIONS

Cantacuzene et al., Tetrahedron Letters, 1966 (20), pp. 2237–2242.

Price et al., J. Am. Chem. Soc., 63, (1941), pp. 2796–2798.

Thyagarajan, Mechanisms of Molecular Migrations, vol. 3, pp. 91–96, (3/30/1971).

McDonald et al., J. Org. Chem., 35, (1970) pp. 2942–2947.

*Primary Examiner*—Anton H. Sutto
*Assistant Examiner*—Michael Shippen
*Attorney, Agent, or Firm*—John T. Reynolds

[57] ABSTRACT

This invention relates to new and novel processes for the production of carboxylic acids from glycidonitriles in high yields and high purity. The processes are especially useful for the preparation of 2-(p-isobutylphenyl)propionic acid, (Ibuprofen), also known as Motrin, a known and highly active antiinflammatory agent as well as a host of other carboxylic acids which are known in the art as useful compounds.

2 Claims, No Drawings

PROCESSES FOR THE PRODUCTION OF CARBOXYLIC ACIDS FROM GLYCIDONITRILES

This is a division of application Ser. No. 271,389, filed July 13, 1972, now abandoned.

BACKGROUND OF THE INVENTION

Prior art carboxylic acid syntheses from aromatic ketones by the addition of hydrogen cyanide such as disclosed by Eliel et al. Org. Syn. 33, 7 (1953) involve a reversible step with an unfavorable equilibrium as well as a reduction step. In the processes of the present invention the steps are irreversible and no reduction step is required. The processes of the present invention thus result in greatly increased yields and higher purity of the desired carboxylic acid. The carboxylic acids which are produced by the processes of this invention are known in the art as useful compounds. For example, 2-(p-isobutylphenyl)propionic acid and 2-m-fluoro-p-phenyl)phenylpropionic acid are highly active antiinflammatory agents, and 3,4-dimethoxyphenylacetic acid is useful in preparing papaverine.

SUMMARY OF THE INVENTION

The novel processes of this invention are illustratively represented by the following reaction sequences:

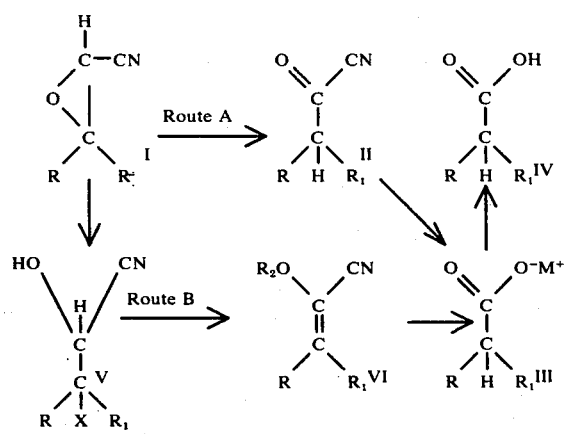

wherein in the above formulae when taken separately R represents hydrogen, an aliphatic, alicyclic, aromatic or heterocyclic group and $R_1$ when taken separately represents an aliphatic, alicyclic, aromatic or heterocyclic group; R and $R_1$ when taken together and connected represent an alicyclic or heterocyclic group, $R_2$ is alkyl, aralkyl or alkenyl such as those hereinafter defined under the definitions of R and $R_1$ below, or the acyl radical of an organic carboxylic acid such as those hereinafter defined; $M^+$ is an alkali metal selected from the group consisting of sodium, potassium and lithium; and X is selected from the group consisting of chloro, bromo and iodo.

Included among the aliphatic, alicyclic and aromatic groups which R and $R_1$ can each represent when taken separately are, for example, alkyl (including saturated and unsaturated, straight and branched chain alkyl and cycloalkyl) and aryl (including alkaryl and aralkyl) radicals, such as methyl, ethyl, propyl, isopropyl, n-butyl, sec. butyl, tert. butyl, amyl, hexyl, heptyl, octyl, decyl, dodecyl, octadecyl, vinyl, allyl, methallyl, butenyl, pentenyl, hexenyl, heptenyl, octenyl, ethylnyl, propynyl, butynyl, pentynyl hexynyl, heptynyl, octynyl and isomeric forms thereof, cyclobutyl, cyclopentyl, cyclohexyl, methylcyclohexyl, cycloheptyl, cyclooctyl, cyclodecyl, cycloundecyl, cyclododecyl, cyclopentadecyl, phenyl, tolyl xylyl, benzyl, phenethyl, phenylpropyl, benzhydryl, naphthymethyl, o-carboxylbenzyl, and the like, as well as fused and bridged rind structures, such indanyl, indenyl, naphthyl, acenaphtyl, phenanthryl, cyclopentanopolyhydrophenanthryl, adamantanyl, bicyclo[3:1:1]heptyl, bicyclo[2:2:2]octyl and the like; all of which can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like; nitro groups; amino groups; alkylamino groups, such as methylamino, ethylamino, dimethylamino and the like; halogens, such as fluorine, chlorine, or bromine; carbonyl derivatives such as enol ethers and ketals; and the like.

Included among the heterocyclic groups which R and $R_1$ can represent are substituted and unsubstituted azabicycloalkane groups such as azabicyclo [3.2.2] octyl and azabicyclo [3.2.1] nonyl and the like, furfuryl groups, tetrahydrofurfuryl groups, piperidyl groups, pyrrolidyl groups, pyridyl groups, thiophene grous, alkaloid nuclei groupings containing for example indole, dihydroindole, quinolidine, quinthio groups and the like.

Included among the alicyclic and heterocyclic groups in which $R_1$ and $R_2$ when taken together and connected can represent, are cyclopropyl, cyclobutyl, cyclohexyl, dicyclohexyl, cyclodecyl, cyclododecyl, cyclopentadecyl, and the (like) piperidyl, pyrrolidyl, and the like; fused ring systems such as cyclopentanopolyhydrophenanthranyl, indanyl, indenyl, and the like, bridged ring systems such as adamantyl, bicyclo [2.2.1] heptyl, bicyclo [2.2.2] octyl, bicyclo (3.2.2) nonyl, azabicycloalkyls, and the like all of which can be substituted by non-interfering substituents such as those hereinbefore named.

Certain of the intermediated falling within the scope of formula VI, above, exist in either the cis configuration, the trans configuration or mixtures thereof. However, for the purpose of carrying out the process of this invention the stereo configuration of the compounds of formula VI is not important since both the cis and trans forms react in the subsequent process steps of this invention to produce the desired products (IV).

The compounds of formula II, above, are known to dimerize under certain conditions as shown by the following sequence of formulae:

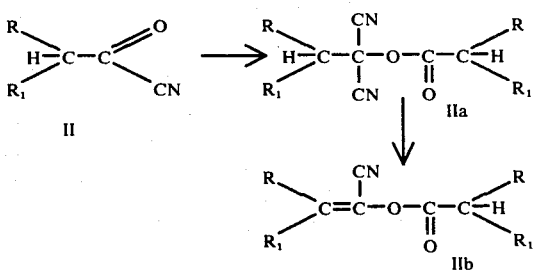

wherein R and $R_1$ have the same meanings given above. For simplicity the compounds of formula II will be referred to in terms of their monomeric structure (II). For the purpose of this invention, their particular structure is not important since all forms react in the subsequent process steps to produce the desired carboxylic acids (IV).

DETAILED DESCRIPTION OF THE INVENTION

The starting glycidonitriles of formula I are either known in the art or can be prepared from known ketones and aldehydes by a Darzens condensation, for example in accordance with the procedure disclosed by V. F. Martynov and A. V. Schelkunov, J. Gen. Chem. USSR 27, 1271–3 (1957). In preparing the necessary starting materials, a ketone or aldehyde of formula VII;

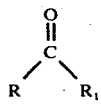

VII wherein R and $R_1$ have the same meanings given above, is reacted with chloroacetonitrile in the presence of a strong base such as sodium methoxide, potassium t-butoxide, sodium t-amylate and the like. The reaction is carried out in a non-polar aprotic solvent such as xylene, toluene, hexanes, petroleum ethers and the like, preferably at a relatively low temperature, such as from about −10° to about +10° C., for a period of from about 1 to 5 hours. The glycidonitrile (I) thus obtained is recovered and purified by conventional methods, for example, by distillation under reduced pressure.

Route A

In carrying out the process of Route A of this invention, the glycidonitriles of formula I are subjected to the following reaction steps:

IA. The selected glycidonitrile (I) is dissolved or suspended in a suitable inert organic solvent, for example, hexanes, petroleum ethers, diethylether, xylene, toluene and the like, relatively high boiling solvents such as xylene, toluene, high boiling petroleum ethers, e.g., Skellysolve V, and the like or mixtures thereof, are advantageous. The solution thus obtained is then treated with a Lewis acid which has a non-nucleophilic anion, such as potassium bisulfate, lithium trifluoroacetate, lithium perchlorate, lithium, tetrafluoroborate, lithium sulfate, and the like. Lithium perchlorate is preferred. The time required for rearrangement of the glycidonitriles of formula I to obtain the corresponding 2-oxopropionitrile of formula II is dependent in part on the temperature at which the reaction is carried out, a temperature between about 100° C. to about 160° C. is preferably employed (reflux temperature is advantageous) for a period of from about a few minutes to about 24 hours for completion of the reaction. For example, at 110° C. about 16 to 24 hours are required whereas at 140° C. 3 to 4 hours is generally sufficient for completion of the reaction. The compounds of formula II thus obtained can be recovered from the reaction mixture and purified by conventional methods, for example, chromotography and/or crystallization from a suitable solvent such as methylene chloride, ethylacetate, xylene, toluene, hexanes, toluene, benzene and the like or by distillation under reduced pressure. Alternatively, the compounds of formula II are used directly in the next step without recovery from the reaction medium.

2A. The compounds of formula II thus obtained are then subject to hydrolysis under basic conditions, preferably in the presence of an alkali metal base such as sodium hydroxide, potassium hydroxide, lithium hydroxide, sodium carbonate, potassium bicarbonate and the like to give the alkali metal salt of the corresponding carboxylic acid (III). The hydrolysis is carried out within a broad temperature range, for example from about 0° C. to about 100° C., for a period of from about 1 to about 24 hours, however, temperatures within the range of from about 40° to 80° C. are preferred. The carboxylic acid salt (III) thus obtained is recovered and purified by conventional methods as described in Step IA, above, or the salt is used in the next step without purification. When the sodium salt (III) is a solid, it is often advantageous to recover the salt from the reaction mixture by crystallization prior to acidification since it results in higher purity of the desired free carboxylic acid (IV).

3A. The sodium salt (III) thus obtained is then subjected to acidification with a strong acid, for example, hydrochloric acid, sulfuric acid, phosphoric acid, trifluoroacetic acid, p-toluenesulfonic acid, benzenesulfonic acid, methanesulfonic acid and the like, to obtain the corresponding free acid (IV). The acidification is carried out within a broad temperature range such as from about 0° C. or lower to the boiling point to the reaction mixture. The product (IV), thus obtained, is recovered from the reaction mixture and purified by conventional methods, for example, the product is extracted from the reaction mixture in a suitable organic solvent such as Skellysolve B hexanes, toluene, xylene, ethyl acetate, benzene, methylene chloride, chloroform and the like and crystallized, if the product is a solid. If the product is a liquid it is recovered and purified by distillation, preferably at reduced pressure.

Route B

In carrying out the process of Route B of this invention the glycidonitriles of formula I are subjected to the following reaction steps:

IB. The selected glycondonitrile is dissolved or suspended in a suitable inert organic solvent such as those named in Step IA, above, and treated with a hydrogen halide selected from the group consisting of hydrogen chloride, hydrogen bromide, and hydrogen iodide to obtain the corresponding 2-hydroxy-3-halopropionitrile (V). In carrying out the reaction the hydrogen halide can be used under anhydrous or aqueous conditions. In the preferred embodiment, the hydrogen halide is used in a slight excess of the theoretically required amount. Anhydrous conditions are preferred. The reaction period is from about 1 to 8 hours, depending on the particular starting material employed and the temperature at which the reaction is carried out. Temperatures of from about 20° C. to about 60° C. are generally preferred, by the reaction is operative at higher and lower temperatures. When the reaction is carried out under aqueous conditions the aqueous phase is removed and the organic phase containing the intermediate compound V is dried by conventional methods, for example, by azeotripic distribution or over a drying agent such as anhydrous sodium sulfate etc, magnesium sulfate, sodium carbonate and the like. When anhydrous conditions are employed, compound V is used directly in the next step without isolation from the reaction medium.

2B. The 2-hydroxy-3-halopropionitrile (V) is then subjected to acylation and dehydrohalogenation in accordance with procedures well known in the art to obtain the corresponding enol acylates of formula VI. For example, the selected compound V is treated with excess acid anhydride or acid halide at about room temperature for a period of from about 1 to about 24 hours in the presence of a tertiary amine such as pyridine, triethyl amine, lutidine, N-methylmorpholine, N,N-dimethylaniline and the like. Suitable acylating agents are the acid anhydrides or acid halides of organic carboxylic acids containing from 1 to 18 carbon atoms; for example, saturated and unsaturated aliphatic acids and aromatic acids such as acetic, propionic, butyric, isobutyric, tert.-butylacetic, valeric, isovaleric, caproic, caprylic, decanoic, dodecanoic, acrylic, crotonic, hexynoic, heptnoic, octynoic, cyclobutanecaboxylic, cyclopentanecarboxylic, cyclopentenecarboxylic, cyclohexanecarboxylic, dimethylcyclohexanecarboxylic, benzoic, toluic, naphthoic, ethylbenzoic, phenylacetic, naphthaleneacetic, phenylvaleric, cinnamic, phenylpropiolic, phenylpropionic, p-butoxyphenylpropionic, succinic, glutaric, dimethylglutaric, maleic, cyclopentylpropionic, myristic, palmitic and stearic acids. The dehydrohalogenation is carried out by adding an excess of anhydrous base following the acylation step. Bases which can be used include the tertiary amines disclosed above as esterification catalysts, as well as other bases such as sodium hydride, sodium amide, sodium methoxide, potassium ethoxide, sodium t-butoxide, sodium t-amylate and the like. In the preferred embodiment, the dehydration is carried out under reflux temperatures for a period of from about 1 to about 24 hours, or alternatively an excess of the selected base can be added and the dehydration can be carried out simultaneously with the acylation step. The enol acylates of formula VI, thus obtained are, if desired, recovered from the reaction mixture and purified by conventional methods such as those described in step (2A), above, or preferably they are used directly in the next step without recovery from the reaction medium.

3B. The enol acylates VI are then subjected to hydrolysis under basic conditions in the same manner as described in step (2A), above, to obtain the alkali metal salt of the corresponding carboxylic acid (III) which is recovered and purified as described in step 2A, above, or used in the next step without recovery from the reaction medium.

4B. The sodium salt (III) thus obtained is then acidified and recovered in the same manner as described in step (3A), above, to obtain the desired carboxylic acid (IV).

2B-a. Alternatively, the 2-hydroxy-3-halopropionitrile V is subjected to etherification in accordance with methods known in the art of example, with an alkyl, alkenyl or aralkyl halide such as methyl bromide, ethyl chloride, propyl chloride, isopropyl iodide, allyl chloride, 1-propenyl bromide, t-butenylchloride, pentenyl iodide, benzoyl chloride and the like or with dimethyl sulfate or diethylsulfate. The etherification is carried out in the presence of an anhydrous base such as sodium hydride, sodium amide, sodium t-butoxide and the like followed by dehydrohalogenation in the presence of a base to obtain the corresponding enol ether (VI). Dehydrohalogenating agents are those bases listed above as well as the tertiary amines used in the acylation and dehydrogalogenation procedure described hereinabove.

3B-a. The enol ethers (VI) thus obtained are then subjected to acid catalyzed hydrolysis to obtain the 2-oxopropionitriles of formula II. The hydrolysis is carried out in the presence of a catalytic amount of a strong acid such as hydrochloric acid, sulfuric acid, phosphoric acid, trifluoroacetic acid, p-toluenesulfonic acid, benzenesulfonic acid, methanesulfonic acid, and the like, at a temperature within the range of from about $-20°$ to about $160°$ C. for a period of from about 5 minutes to about 24 hours. The compounds of formula II thus obtained are then converted to the carboxylic acids of formula IV, in the same manner as disclosed in steps (2A) and (3A), above.

In both Routes A and B, above, none of the intermediates need to be isolated and purified. The entire process can be conveniently carried out in a one pot operation.

The following Examples illustrate the best mode contemplated by the inventors for carrying out their invention, but are not to be construed as limiting the scope thereof.

EXAMPLE 1

2-(p-isobutylphenyl)propionic acid (IV)

A mixture of 17.6 g. of p-isobutylacetophenone (VII) and 61 ml. of a 15.4% w/v solution of chloroacetonitrile in xylene is cooled to about $-10°$ C. and a solution of sodium t-amylate (prepared by stirring 4.45 g. of sodium amide and 10.0 g. of t-amyl alcohol in 150 ml. of xylene at $60°$ C. for about 4 hours) is added with stirring over a period of about 15 minutes keeping the temperature at about $-5°$ C. Stirring is continued for an additional period of about 1 hour and then 70 ml. of water is added. The reaction mixture is then filtered and the organic (xylene) phase is separated. The aqueous layer is extracted with 30 ml. of xylene and the xylene solutions are combined, dried over anhydrous sodium sulfate and concentrated. The residue thus obtained is distilled ($105°$ C./.05 mm.) to give 18.88 g. (88% yield) of 3-methyl-3-(p-isobutylphenyl)-glycidonitrile (I) as an oil.

A solution of 7.87 g. (36.6 mmole) of the 3-methyl-3-(p-isobutylphenyl)glycidonitrile (I) thus obtained in 60 ml. of toluene is treated with 40 mmole of dry hydrogan chloride (10.7 ml. of 3.71 N HCl in ether) and stirred for about 1 hour to give 2-hydroxy-3-methyl-3-(p-isobutylphenyl)-3-chloropropionitrile (V) as shown by TLC (thin-layer chromatography). The reaction is then treated with 3.64 g. (46 mmole) of pyridine and 4.30 g. (4.22 mmole) of acetic anhydride. The reaction mixture is stirred for about 2½ hours to give the corresponding chloroacetate. Triethylamine [5.04 g. (50 mmole)[ is then added and the mixture is held at reflux for about 20 hours. TLC shows a mixture of the cis and trans isomers of 2-acetoxy-3-methyl-3-(p-isobutylphenyl)acrylonitrile (VI). If desired the intermediate thus obtained can be isolated by washing with aqueous acid and then drying the toluene solution over anhydrous sodium sulfate and concentration at reduced pressure to a mixture of cis and trans isomers of 2-acetoxy-3-methyl-3-(p-isobutylphenyl)acrylonitrile (VI), as an oil, ultraviolet spectrum (methanol), λmax, 212mµ ($\epsilon$=10,730) and 263mµ ($\epsilon$= 13,500); NMR (nuclear magnetic resonance) and IR (infrared) spectra support the structure.

Alternatively, the toluene solution of the intermediate (VI) is diluted with 16 ml. of methanol and 12 ml. of 50% aqueous sodium hydroxide solution and the mixture is stirred at reflux for about 16 hours. The two phases are then separated while warm and the toluene phase is extracted with 25 ml. of aqueous 5% sodium hydroxide solution to give an aqueous alkaline solution containing the sodium salt of 2-(p-isobutylphenyl)propionic acid (III). The aqueous hydroxylic phases are combined, acidified with about 30 ml. of concentrated hydrochloric acid and extracted with two 50 ml. portions of ethyl acetate. The ethyl acetate extracts are combined, dried over anhydrous sodium sulfate, decolorized with 1 g. of activated charcoal (Darco), filtered and concentrated to give 7.57 g. of oil which is diluted with 15 ml. of Skellysolve B hexanes, seeded and cooled at 50° C. for about 2 hours. The crystalline solid thus obtained is collected on a filter and washed with 10 ml. of hexanes to give 4.836 g. of 2-(p-isobutylphenyl)propionic acid (IV), melting at 74.0°–75.5° C.; NMR and IR supports the assigned structure.

Anal. Calcd. for $C_{13}H_{18}O_2$: C, 75.69; H, 8.79; Found: C, 75.82; H, 8.78.

A second fraction obtained from the mother liquors gives 0.712 g. of 2-(p-isobutylphenyl)propionic acid (IV), melting at 73.0°–74.5° C.

EXAMPLE 2

2-(p-isobutylphenyl)propionic acid (IV)

A solution of 3-methyl-3-(p-isobutylphenyl)-glycidonitrile (I) about 60% in toluene, obtained from 0.050 mole of p-isobutylacetophenone (99.5% yield) in accordance with the procedure described in Example 1, above, is diluted with 10 ml. of Skellysolve V petroleum ether and treated with 0.400 g. of lithium perchlorate. The mixture is heated with stirring under nitrogen in a 115° C. oil bath for about 25 hours (reaction time at 122° C. about 17 hours) to give 3-methyl-3-(p-isobutylphenyl-2-oxoproprionitrile (II). The reaction mixture is cooled to about 70° C., diluted with 30 ml. of toluene and 10 ml. of water, treated with 8.0 ml. of aqueous 50% sodium hydroxide and then 60 mg. of catalin is added and the mixture stirred at 75° C. for 4 hours. The reaction is diluted with 15 ml. of acetone and cooled to about 0° C. with stirring. The crystalline salt thus obtained is collected on a filter, washed with toluene and then with cold acetone to give the sodium salt of 2-(p-isobutylphenyl)-propionic acid (IV).

The sodium salt thus obtained is then taken up in 70 ml. of Skellysolve B hexanes and 20 ml. of water and then 10 ml. of 12 N sulfuric acid is added with stirring. The two phases are then separated and the organic (upper) phase is washed with warm water. The combined aqueous phase is washed again with 20 ml. of Skellysolve B hexanes which is backwashed with 20 ml. of water. The organic phases are combined, dried over anhydrous sodium sulfate, concentrated to about 18 ml. of allowed to crystallize. The solid thus obtained is collected on a filter and washed with cold Skellysolve B hexanes to give 7.42 g. (72% yield) of 2-(p-isobutylphenyl)propionic acid (IV); m.p. 73°–74.1° C.; $\mu$max (CH$_3$OH) 263 and 272m$\mu$; IR and NMR spectra support the assigned structure.

Following the procedure of Examples 1 and 2, above, other glycidonitriles of formula (I) can be converted to the corresponding carboxylic acids of formula (IV). The following conversions are representative:

3,4-dihydrospiro[naphthalene-1(2H), 2'-oxirane]-3'-carbonitrile to obtain 1,2,3,4-tetrahydro-1-naphthoic acid, 17β-acetoxyspiro[androstane-3,2'-oxirane]3'-carbonitrile to obtain 17β-acetoxyandrostane-3β-carboxylic acid, spiro[adamantane-2,2'-oxirane]-3'-carbonitrile to obtain 2-adamantanecarboxylic acid, β-phenylcyclohexaneglycidic acid to obtain α-phenylcyclohexaneacetic acid, 3,3-diphenylglycidic acid to obtain diphenylacetic acid, 1,2,3,4-tetrahydrospiro[anthracene-9(10H),2'-oxirane]-3'-carbonitrile to obtain 1,2,3,4,9,10-hexahydro-9-anthroic acid, tetrahydrospiro[oxirane-2,4'-[4H]pyran]3-carbonitrile to obtain tetrahydro-4H-pyran-4-carboxylic acid, and spiro[1H-2-benzopyran-4(3H),2'-oxirane]-3'-carbonitrile to obtain 3,4-dihydro-1H-2-benzopyran-4-carboxylic acid.

EXAMPLE 3

2-(p-isobutylphenyl)propionic acid (IV)

Following the procedure of Example 2, above, but substituting a stiochiomeric equivalent amount of fused potassium bisulfate in place of lithium perchlorate gives 2.31 g. (22.4% yield) of 2-(p-isobutylphenyl)propionic acid (IV).

EXAMPLE 4 cyclohexanecarboxylic acid (IV)

A solution of 19.6 g. of cyclohexanone (VII) and 16.5 g. of chloroacetonitrile in toluene is cooled with stirring to about −10° C. and treated dropwise with a solution of sodium t-amylate (prepared by stirring 8.58 g. of sodium amide, 19.3 g. of t-amyl alcohol and 300 ml. of toluene for 2 hours at 50° C.) over a period of about 45 minutes, keeping the reaction temperature at about −10° to about −5° C. After the addition is complete the reaction mixture is stirred for about 1 hour at about 0° C., diluted with 100 ml. of water and allowed to separate. The aqueous phase is removed and extracted with 50 ml. of toluene, The toluene (organic) phases are combined, washed with brine, dried ovr anhydrous sodium sulfate and concentrated to give 24.4 g. (89% yield) of the corresponding glycidonitrile, 1-acaspiro[2,5]octane-2-carbonitrile, (I) as an oil.

A solution of 6.84 g. of the glycidonitrile (I) thus obtained in 40 ml. of toluene is treated with dry hydrogen chloride (14.6 ml. of 3.71 N hydrogen chloride in ether), stirred at about 26° C. for 4 hours and then at 45° C. for an additional 2.5 hours to give 1-chlorocyclohexaneglycolonitrile (V). The reation mixture is then treated with 4.97 g. of pyridine, 4.47 ml. of acetic anhydride and 9.45 ml. of triethylamine and stirring is continued keping the temperature at about 75° C. for about 16 hours. The reaction mixture is then cooled, washed with two 40 ml. portions of 2N hydrochloric acid and then with water. The toluene is then removed and the product distilled to give an 87% yield of the corresponding 2-actoxyacrylonitrile (VI) ($\Delta^1$-cyclohexaneglycolonitrile, acetate) b.p. 89°–94° C./0.6 mm. Hg.; IR and NMR spectra support the assigned structure.

Alternatively the toluene solution obtained above is mixed with 15 ml. of water, 6 ml. of acetone and 12 ml. of aqueous 50% sodium hydroxide solution and stirred overnight at about 50° C. to give the sodium salt of cyclohexanecarboxylic acid (III). The reaction mixture is then cooled and the phases separated. The toluene phase is washed with 10 ml. of 5% aqueous sodium hydroxide. The alkaline phase and wash are combined, backwashed with 25 ml. of toluene, acidified with about 17 ml. of 12 N sulfuric acid and extracted with Skellysolve B hexanes (2 × 50 ml.). The combined extracts are dried over anhydrous sodium sulfate, concentrated and the residue is distilled (154°–159° C./54 mm. Hg.) to give 4.382 g. (64% yield) of cyclohexanecarboxylic acid (IV), IR and NMR spectra are identical with those of an authentic sample of cyclohexanecarboxylic acid.

EXAMPLE 5

2-methylvaleric acid (IV)

A solution of 17.2 g. of 2-pentanone (VII) and 16.5 g. of chloroacetonitrile in 20 ml. of toluene is treated with sodium t-amylate and worked up in the manner described in Example 3, above, to give a toluene solution of the corresponding glycidonitrile (I) (2-methyl-2-n-propylglycidonitrile).

The toluene solution thus obtained is treated with dry hydrogen chloride (59.3 ml. of 3.71 N HCl in ether) with stiring for about 4 hours at 45° C. A mixture of 21.1 g. of pyridine, 18.2 ml. of acetic anhydride and 38.5 ml. of triethyl amine is then added and the reaction mixture is stirred at 75° C. for about 16 hours. The reaction mixture is then cooled, washed with 2 N hydrochloric acid (2 × 160 ml.) and then with 100 ml. of water. The intermediate thus obtained can if desired be isolated by drying and concentrating the toluene solution or alternatively, the toluene solution is mixed with 61 ml. of water, 24 ml. of acetone and 48 ml. of aqueous 50% sodium hydroxide solution and stirred at about 50° C. overnight to give the sodium salt of 2-methylvaleric acid (III), the reaction mixture is then cooled and the two phases are separated. The toluene phase is washed with 10 ml. of 5% aqueous sodium hydroxide solution. The alkali phase and wash are combined and backwashed with 25ml. of toluene. The alkaline phase is then acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give 17.4 g. (75% yield) of 2-methylvaleric acid (IV), b.p. 186° C./760 mm. Hg.

EXAMPLE 6

3,4-dimethoxyphenylacetic acid (IV)

A solution of 33.1 g. of 3,4-dimethyloxybenzaldehyde (VII) and 16.5 g. of chloroacetonitrile in 20 ml. of toluene is treated with sodium t-amylate and worked up in the manner described in Example 3, above, to give a toluene solution of 3-(3,4-dimethoxyphenyl) glycidonitrile (I).

The toluene solution thus obtained is treated with dry hydrogen chloride (59.3 ml. of 3.71 N HCl in ether) with stiring for about 4 hours at 45° C. A mixture of 21.1 g. of pyridine, 18.2 ml. of acetic anhydride and 38.5 ml. of triethyl amine is then added and the reaction mixture is stirred at 75° C. for about 16 hours. The reaction mixture is then cooled, washed with 2 N hydrochloric acid (2 × 160 ml.) and then with 100 ml. of water. The intermediate 2-acetoxy-3-(3,4-dimethoxyphenyl)acrylonitrile (VI) thus obtained, can if desired be isolated by drying and concentrating the toluene solution. Alternatively, the toluene solution is mixed with 61 ml. of water, 24 ml. of acetone and 48 ml. of aqueous 50% sodium hydroxide solution and stirred at about 50° C. overnight to give the sodium salt of 3,4-dimethoxyphenylacetic acid (III). The reaction mixture is then cooled and the two phases are separated. The toluene phase is washed with 10 ml. of 5% aqueous sodium hydroxide solution. The alkaline phase and wash are combined and backwashed with 25 ml. of toluene. The alkaline phase is acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give 31.3 g. (80% yield) of 3,4-dimethoxyphenylacetic acid (IV), m. p. 96°–98° C.

EXAMPLE 7 hexanoic acid

A solution of 17.2 g. of valeraldehyde (VII) and 16.5 g. of chloroacetonitrile in 20 ml. of toluene is treated with sodium t-amylate and worked up in the manner described in Example 3, above, to give a toluene solution of 3-butylglycidonitrile (I).

The toluene solution thus obtained is treated with dry hydrogen chloride (59.3 ml. of 3.71 N HCl in ether) with stirring for about 4 hours at 45° C. A mixture of 21.1 g. of pyridine, 18.2 ml. of acetic anhydride and 38.5 ml. of triethyl amine is then added and the reaction mixture is stirred at 75° C. for about 17 hours. The reaction mixture is then cooled, washed with 2 N hydrochloric acid (2 × 160 ml.) and then with 100 ml. of water. The intermediate 2-acetoxy-3-butylacrylonitrile (2-acetoxy-2-heptenonitrile) (VI) thus obtained can if desired be isolated by drying and concentrating the toluene solution or alternatively, the toluene solution is mixed with 61 ml. of water, 24 ml. of acetone and 48 ml. of aqueous 50% sodium hydroxide solution and stirred at about 50° C. overnight to give the sodium salt of hexanoic acid (III). The reaction mixture is then cooled and the two phases are separated. The toluene phase is washed with 10 ml. of 5% aqueous sodium hydroxide solution. The alkaline phase and wash are combined and backwashed with 25 ml. of toluene. The alkaline phase is acidified with 12 N sulfuric acid and extracted with Skellysolve B hexanes, (2 × 50 ml.). The hexane extracts are combined and dried over anhydrous sodium sulfate; the solvent is removed and the product distilled under vacuum to give 15.3 g. (66% yield) of hexanoic acid (IV).

EXAMPLE 8

2-(m-fluoro-p-phenyl)phenylpropionic acid

Following the procedure of Example 1 or 2, above, but substituting a stoichiometric equivalent amount of m-fluoro-p-phenylacetophenone (VII) as starting material in place of p-isobutylacetophenone gives 2-methyl-2-(m-fluoro-p-phenyl) phenylglycidonitrile (I) which is converted by the procedure of either Example 1 or 2 (Rote A or B) to obtain 2-(m-fluoro-p-phenyl)-phenylpropionic acid (IV).

I claim:

1. The process for the production of a carboxylic acid of the formula:

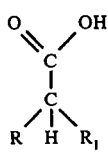

wherein R when taken separately represents hydrogen or an aliphatic, alicyclic, aromatic or heterocyclic group and $R_1$ when taken separately represents an aliphatic, alicyclic, aromatic or heterocyclic group; and R and $R_1$ when taken together and connected represents an alicyclic or heterocyclic group, which comprises:
1. treating a glycidonitrile of the formula:

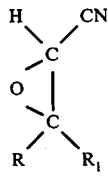

wherein R and $R_1$ have the meanings given, above, with a hydrogen halide selected from the group consisting of hydrogen chloride, hydrogen bromide, and hydrogen iodide to obtain a 2-hydroxy-3-halopropionitrile of the formula:

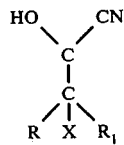

wherein R and $R_1$ have the same meanings as given, above, and X is selected from the group consisting of chloro, bromo or iodo;
2. etherifying with an alkyl, alkenyl or aralkyl halide or with dimethylsulfate or diethylsulfate in the presence of anhydrous base and dehydrohalogenating the 2-hydroxy-2-halopropionitrile thus obtained to obtain an enol ether of the formula

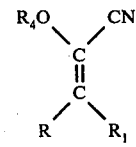

wherein R and $R_1$ have the meanings given, above, and $R_4$ is selected from the group consisting of alkyl, aralkyl and alkenyl;
3. subjecting the enol ether so obtained to an acid catalyzed hydrolysis with a strong acid to obtain a 2-oxopropionitrile of the formula

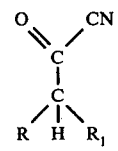

wherein R and $R_1$ have the meanings given, above;
4. subjecting the 2-oxopropionitrile so obtained to hydrolysis with an aqueous alkali metal base to obtain an alkali metal salt of a carboxylic acid of the formula:

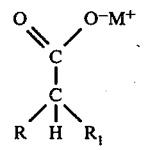

wherein R and $R_1$ have the meanings given, above, and $M^+$ is selected from the group consisting of sodium, potassium, and lithium, and
5. acidifying the alkali metal salt of the carboxylic acid so obtained with a mineral acid to obtain the corresponding free carboxylic acid.

2. A process as defined in claim 1, wherein R is p-isobutylphenyl and $R_1$ is methyl.

* * * * *